(12) United States Patent
Peppas et al.

(10) Patent No.: US 7,771,732 B2
(45) Date of Patent: Aug. 10, 2010

(54) POLYMER NETWORK COMPOSITIONS AND ASSOCIATED METHODS

(75) Inventors: Nicholas A. Peppas, Austin, TX (US); James Z. Hilt, Lexington, KY (US); Mark E. Byrne, Auburn, AL (US)

(73) Assignee: Board of Regents, The University of Texas System, Austin, TX (US)

( * ) Notice: Subject to any disclaimer, the term of this patent is extended or adjusted under 35 U.S.C. 154(b) by 1139 days.

(21) Appl. No.: 11/380,803

(22) Filed: Apr. 28, 2006

(65) Prior Publication Data

US 2007/0071712 A1    Mar. 29, 2007

Related U.S. Application Data

(60) Provisional application No. 60/675,811, filed on Apr. 28, 2005.

(51) Int. Cl.
*A61K 9/00* (2006.01)
(52) U.S. Cl. .................................................. 424/400
(58) Field of Classification Search ...................... None
See application file for complete search history.

(56) References Cited

U.S. PATENT DOCUMENTS

| 6,458,599 B1 | 10/2002 | Huang |
| 6,680,210 B2 | 1/2004 | Huang |
| 6,979,573 B2 | 12/2005 | Huang |
| 2002/0071869 A1 | 6/2002 | Bures et al. ................. 424/487 |
| 2004/0192869 A1 | 9/2004 | Kulkarni et al. ............. 526/264 |
| 2006/0030027 A1 | 2/2006 | Ellson et al. |
| 2007/0190084 A1* | 8/2007 | Hilt et al. .................... 424/400 |

OTHER PUBLICATIONS

International Search Report and Written Opinion of PCT/US2006/016425 dated Jan. 18, 2007.
Peppas, et al., "New Biomaterials for Intelligent Biosensing, Recognitive Drug Delivery and Therapeutics," B.T. Gattefosse (2003), 96:25-38.
G. Wulff, Molecular imprinting in cross-linked materials with the aid of molecular templates—a way towards artificial antibodies, Angew. Chem. Int. Ed. Engl. 34 pp. 1812-1832, 1995.
K. Mosbach, O. Ramstrom, The emerging technique of molecular imprinting and its future impact on biotechnology, Biotechnology 14 pp. 163-170, 1996.
B. Sellergren, Noncovalent molecular imprinting: antibody-like molecular recognition in polymeric network materials, Trends Anal. Chem. 16 pp. 310-320, 1997.
N. Peppas et al., Physicochemical Foundations and Structural Design of Hydrogels in Medicine and Biology, Annu. Rev. Biomed. Eng., pp. 9-29, 2000.
W. Wizeman et al., Molecularly imprinted polymer hydrogels displaying isomerically resolved glucose binding, Biomaterials 22, pp. 1485-1491, 2001.

(Continued)

*Primary Examiner*—Eric E. Silverman
(74) *Attorney, Agent, or Firm*—Edwin S. Flores; Chainey P. Singleton; Chalker Flores, LLP

(57) ABSTRACT

Biomimetic polymer networks comprising a heteropolymer network having a cavity, the cavity having a selective affinity for a moiety, methods for making biomimetic polymer networks, and methods for using biomimetic polymer networks.

8 Claims, 17 Drawing Sheets

OTHER PUBLICATIONS

M. Byrner et al., Molecular imprinting with hydogels, Advanced Drug Delivery Reviews, pp. 150-161, 2002.

M. Byrne et al., Networks for Recognition of Biomolecules: Molecular Imprinting and Micropatteming Poly (ethylene glycol)-Containing Films, Polymer for Advanced Technologies 13, pp. 798-816, 2002.

S. Zimmerman et al., Synthetic hosts by monomolecular imprinting inside dendrimers, Nature vol. 418, pp. 399-403, 2002.

R. Langer, N.A. Peppas, Advances in biomaterials, drug delivery, and bionanotechnology, AIChEJ 49 pp. 2990-3006, 2003.

P. Parmpi, Biomimetic glucose recognition using molecularly imprinted polymer hydrogels, Biomaterials 25, pp. 1969-1973, 2003.

N. Peppas et al., Biomimetic materials and micropatterned structures using iniferters, Advanced Drug Devlivery Reviews 56, pp. 1587-1597, 2004.

Lei Ye et al., The Development of Artificial Antibodies By Molecular Imprinting, Pure and Applied Biochemistry, Chemical Center, Lund University, 12 pages.

J. Hilt et al., Configurational biomimesis in drug delivery: molecular imprinting of biologically significant molecules, Advanced Drug Delivery Reviews 56, pp. 1599-1620, 2004.

Editor: N. Peppas, Intelligent therapeutics: biomimetic systems and nanotechnology in drug delivery, Advanced Drug Delivery Reviews 56, pp. 1529-1531, 2004.

* cited by examiner

GLUCOSE (A)

(B)

(A)

(B)

(A)

(B)

(C)

(A)

(B)

(C)

(A)

(B)

(C)

2-NBDG

Streptozotocin

POLYMER NETWORK COMPOSITIONS AND ASSOCIATED METHODS

CROSS-REFERENCE TO RELATED APPLICATION

This Application claims the benefit under 35 U.S.C §119 of U.S. Provisional Application No. 60/675,811, filed Apr. 28, 2005.

STATEMENT OF GOVERNMENT INTEREST

This disclosure was developed at least in part using funding from the National Science Foundation, Grant Numbers CTS-03-29317 and DGE-03-33080, and National Institutes of Health, Grant Number EB000246-13A. The U.S. government may have certain rights in the invention.

BACKGROUND

The present disclosure generally relates to polymer compositions, methods of forming such polymer compositions, and methods of using such compositions. These compositions and have improved properties that make them useful for a variety of applications; in particular, the loading and delivery of therapeutic agents.

Recognition in nature is a complex orchestration of numerous interactions between individual atoms and cumulative interactions between secondary structures. For example, the active sites of enzymes are composed of several amino acid residues, which noncovalently bind ligand molecules in a very specific manner. However, the activity of the site is dependent on the stabilization of the three-dimensional structure by the interactions of hundreds of other residues within the structure of secondary and tertiary domains.

The term configurational biomimesis refers to the three-dimensional arrangement of chemical groups that can specifically bind a biomolecule via noncovalent forces. This designed recognition involves analyzing the molecular basis of recognition in biological systems and attempts to mimic similar interactions on a molecular level. For example, analysis of biological systems such as enzyme-substrate, receptor-ligand, antibody-antigen, complementary DNA or RNA strands and protein-protein complexes, etc., can yield much information on the type, number, and arrangement of noncovalent chemical forces needed for aqueous recognition.

Configurational biomimesis is, therefore, a subset of molecular imprinting, which produces precise polymer architectures that can selectively recognize molecules and at times, depending on the matrix structure, differentiate with isomeric specificity.

The concept of molecular imprinting manifests itself from two major synergistic effects, (i) shape specific cavities or nanovacuoles that match the template molecule and (ii) chemical groups orientated to form multiple complexation points with the template molecule. In terms of selectivity, the resulting polymer networks are selective due to the particular chemistry of the binding site, the orientation of the chemistry, as well as by the size and shape of the site for the template molecule.

The quality of the receptor mechanism of imprinted polymers can be assessed via a number of parameters. The significant parameters in determining how well a polymeric network can recognize a given molecule are binding affinity (i.e., the equilibrium association or dissociation constant between the ligand molecule and the network), selectivity (i.e., the ability to differentiate between the ligand and other molecules), and the binding capacity (i.e., the maximum ligand bound per mass or volume of polymer). To a lesser extent, binding or imprinting ratios (i.e., the ratio of recognitive network template bound compared to control network) highlights the recognition properties at a specific concentration.

Binding affinity is a measure of how well the template molecule is attracted to the binding site or how well a ligand binds or is held to the receptor macromolecule. Considering equilibrium theory of receptor-ligand interactions, the dissociation constant, $K_d$, provides a quantitative measure of this level of attraction.

SUMMARY

According to one embodiment, the present disclosure provides biomimetic polymer networks comprising a heteropolymer network having a cavity, the cavity having a selective affinity for a moiety.

According to another embodiment, the present disclosure provides biomimetic polymer networks formed by a process comprising polymerizing a mixture comprising monomers and crosslinkers in the presence of a moiety for which a molecular imprint is to be produced, thereby forming a matrix comprising an imprint of the molecule, and separating the moiety from the matrix.

According to another embodiment, the present disclosure provides methods for forming a biomimetic polymer network comprising polymerizing a mixture comprising monomers and crosslinkers in the presence of a moiety for which a molecular imprint is to be produced, thereby forming a matrix comprising an imprint of the molecule, and separating the moiety from the matrix.

According to another embodiment, the present disclosure provides methods for delivering molecules comprising providing a biomimetic polymer network comprising a heteropolymer network having a cavity, the cavity having a selective affinity for a moiety; loading the biomimetic polymer network with a molecule by allowing a moiety present on the molecule to interact with the cavity; delivering the biomimetic polymer network to a desired location; and providing conditions that reduce the affinity of the cavity for the moiety a sufficient amount to release the molecule.

The features and advantages of the present disclosure will be readily apparent to those skilled in the art upon a reading of the description of the embodiments that follows.

FIGURES

Some specific example embodiments of this disclosure may be understood by referring, in part, to the following description and the accompanying drawings.

Figure 1:
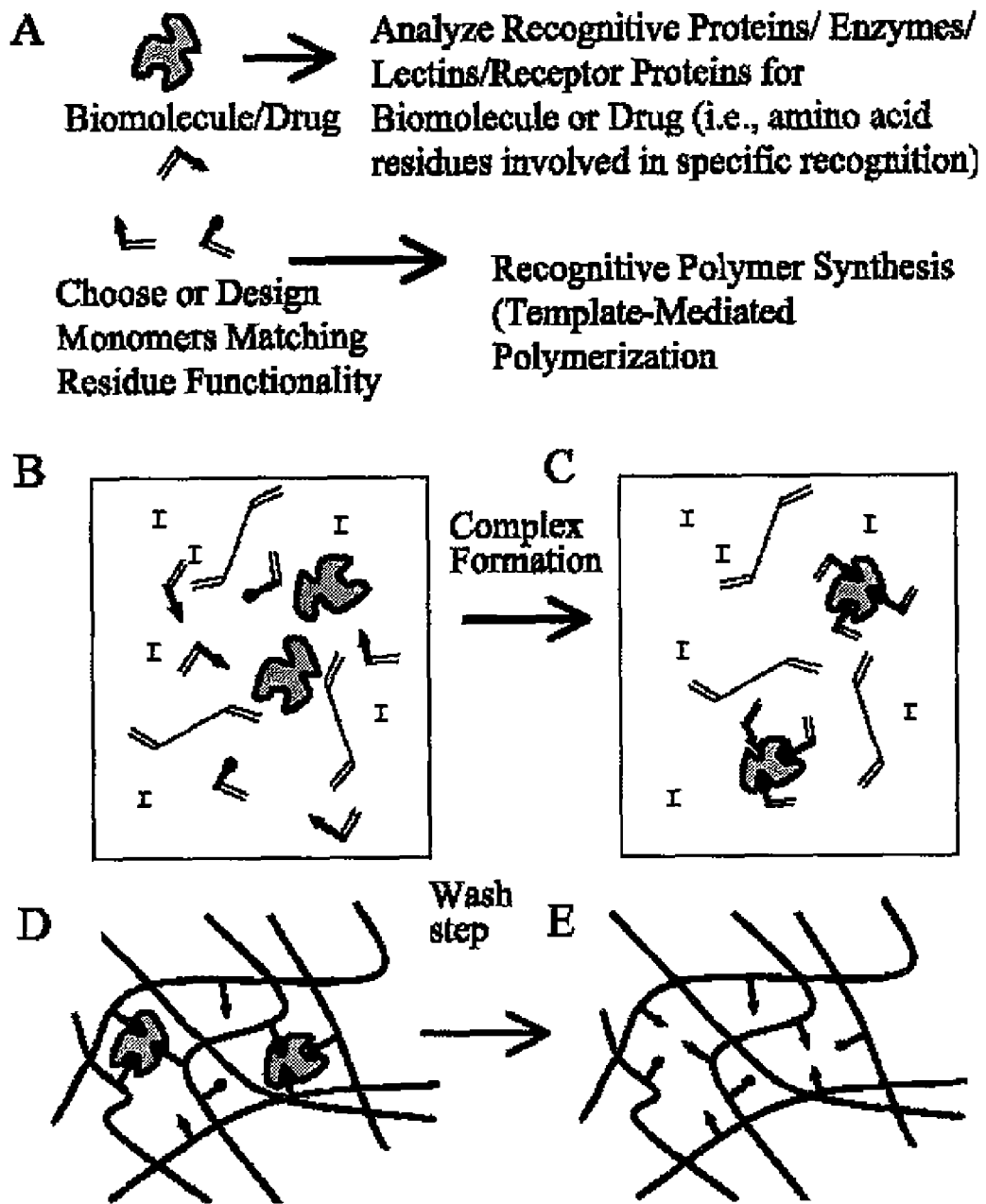
FIG. 1 is a drawing depicting the steps for conformational biomimetic imprinting.
Figure 2:
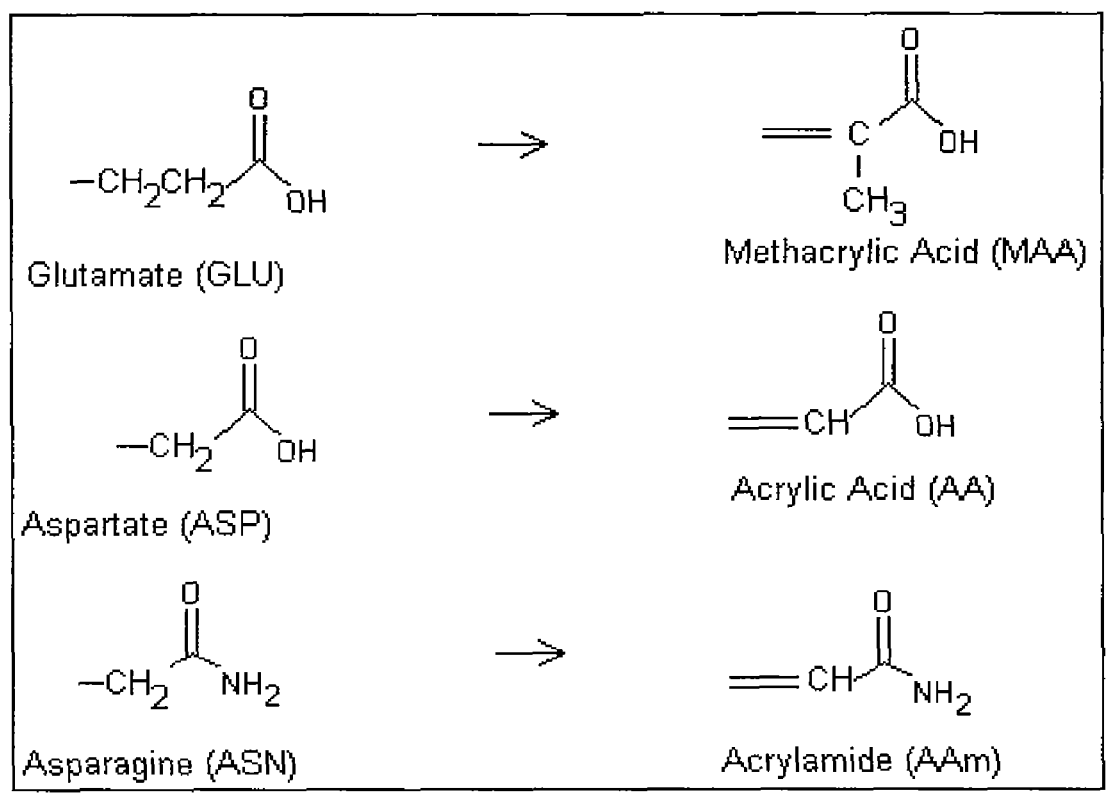
FIG. 2 is a drawing of amino acid residues.

While the present disclosure is susceptible to various modifications and alternative forms, specific example embodiments have been shown in the figures and are herein described in more detail. It should be understood, however, that the description of specific example embodiments is not intended to limit the disclosure to the particular forms disclosed, but on the contrary, this disclosure is to cover all modifications and equivalents as illustrated, in part, by the appended claims.

DESCRIPTION

The present disclosure generally relates to biomimetic polymer network compositions, methods of forming such polymer compositions, and methods of using such compositions. These compositions and have improved properties that make them useful for a variety of applications; in particular, the loading and delivery of therapeutic agents.

The biomimetic polymer networks of the present disclosure generally comprise a polymer network having architectures that have selective affinity for a moiety. Such biomimetic polymer networks may have shape specific cavities that match the moiety, as well as chemical groups oriented to form multiple complexation points with the moiety. In terms of selectivity, the resulting polymer networks are selective due to the particular chemistry of the binding site, the orientation and stabilization of the chemistry in a crosslinked matrix, as well as by the size and shape of the site for the template biomolecule.

In some embodiments, the biomimetic polymer networks may further comprise a moiety. Such compositions may be capable of releasing the moiety in a relatively controlled fashion. The moiety may be present on a target compound, for example, a therapeutic agent. Accordingly, the compositions and methods of the present disclosure may be used in the treatment of a disease. For example, the compositions of the present disclosure may be used as a vehicle to deliver a therapeutic agent to a subject (e.g., a human) in need thereof. The compositions of the present disclosure also may be used to form a medical device or an article. The present disclosure also provides methods of forming a biomimetic polymer network of the present disclosure.

The moiety may be any portion of a molecule recognized by a biomimetic polymer network of the present disclosure. The moiety may be covalently bound to a target compound, for example, a therapeutic agent. In this way, the moiety may be used to associate a target compound with a biomimetic polymer network of the present disclosure. The moiety should either already be present on the target compound or capable of being conjugated to a target compound. Conjugation of moieties to therapeutic agents is known in the art, for example, as disclosed in A. Wong and I. Toth, *Curr. Med. Chem.* 8:1123-36 (2001), the relevant disclosure of which is incorporated by reference. Examples of suitable moieties include, but are not limited, to sugars (e.g., glucose), carbohydrates, peptides, and functional groups. A specific example of a therapeutic agent that comprises a moiety is streptozotocin (R. R. Herr, et al., *J. Am. Chem. Soc.* 89:4808-09 (1967)), which has a glucose moiety.

In certain embodiments, the moiety is a sugar. For example, the sugar may be a monosaccharide. Monosaccharides have the chemical formula $(CH2O)n$ and the chemical structure $H(CHOH)nC=O(CHOH)mH$. If n or m is zero, it is an aldose, otherwise it is a ketose. Monosaccharides may include aldoses, trioses (e.g., glyceraldehyde), tetroses (e.g., threose), pentoses (e.g., ribose, xylose), hexoses (e.g. glucose, fructose, mannose, galactose), ketoses, trioses, tetroses, pentoses (e.g., ribulose), hexoses (e.g., fructose). Any of the L and D isomers of a sugar also may be used, although the D isomer may be more preferred for biological applications. Other examples of suitable sugars include polysaccharides. Polysaccharides have a general formula of $Cn(H2O)n-1$ where n is usually a large number up to 500. Disaccharides, such as, for example, sucrose, lactose, maltose, and the like may be used. Yet another example of suitable sugars includes oligosaccharides and low molecular weight carbohydrates (e.g., having a molecular weight no greater than about 2,000 Da). Further, each carbon atom that supports a —OH group (except for the first and last) is chiral, giving rise to a number of isomeric forms all with the same chemical formula.

Specific embodiments may use the following monosaccharides as moieties: Monoses, Dioses, Trioses, Tetroses, Pentoses, Aldo-pentoses, including arabinose, lyxose, ribose, deoxyribose and xylose, Keto-pentoses including ribulose, xylulose, Hexoses including Aldo-hexoses such as allose, altrose, galactose, glucose, gulose, idose, mannose and talose, and Keto-hexoses such as fructose, psicose, sorbose and tagatose, Heptoses including Keto-heptoses such as mannoheptulose and sedoheptulose, Octoses such as octolose, 2-keto-3-deoxy-manno-octonateand Nonoses such as sialose.

Specific embodiments may use mucopolysaccharides. Mucopolysaccharides are long unbranched polysaccharides consisting of a repeating disaccharide unit. This unit consists of an N-acetyl-hexosamine and a hexose or hexuronic acid, either or both of which may be sulfated. Members of this family vary in the type of hexosamine, hexose or hexuronic acid unit they contain e.g. glucuronic acid, iduronic acid, galactose, galactosamine, and glucosamine. They also vary in the geometry of the glycosidic linkage. Specific example polysaccharides that may be used as moieties include: Chondroitin sulphate, Dermatan sulphate, Keratan sulphate, Heparan sulphate, Heparin, sodium heparin, hyaluronic acid and Hyaluronan.

In other embodiments, the moiety may be a lipid or a short amino acid sequence (e.g., a sequence of about twenty amino acids in length). In particular, lectins may be used as a moiety. Lectins are carbohydrate-binding proteins involved in a variety of recognition processes and exhibit considerable structural diversity. A large variability in quaternary association resulting from small alterations in essentially the same tertiary structure is a property exhibited specially by legume lectins. The strategies used by lectins to generate carbohydrate specificity include the extensive use of water bridges, post-translational modification and oligomerization. Other carbohydrate-based structures may be used as moieties may be located at http://www.chem.qmul.ac.uk/iupac/2carb/(accessed Apr. 27, 2006), incorporated by reference herein.

In general the compositions of the present disclosure have enhanced affinities (e.g., impart greater affinity, bound ratios greater than 1) for a chosen moiety, among other things, allowing for increased loading efficiency. Accordingly, the compositions of the present disclosure also may be used to increase the loading of a target compound or control the release rate of a target compound or both. The compositions of the present disclosure also may be used for delivery of a therapeutic agent. For example, the compositions of the present disclosure may be used as an excipient or as a vehicle for a therapeutic agent. Specifically, higher quantities of a therapeutic agent having a moiety can be loaded within the biomimetic polymer networks of the present disclosure, therefore enabling for higher doses to be loaded. The release of a moiety may be tailored to give a desired release profile, for example, for sustained release of a therapeutic agent. Thus, when the moiety is bound to a therapeutic agent, treatment with the therapeutic agent may be optimized.

Example therapeutic agents include water soluble or poorly soluble drug of molecular weigh from 40 to 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

The compositions of the present disclosure may be formed using configurational biomimetic imprinting (FIG. 1). Configuration biomimetic imprinting techniques generally involve forming a prepolymerization complex between the template molecule (e.g., a moiety) and functional monomers or functional oligomers (or polymers) with specific chemical structures designed to interact with the template either by covalent chemistry or noncovalent chemistry (self-assembly) or both. Once the prepolymerization complex is formed, the polymerization reaction occurs in the presence of a crosslinking monomer and an appropriate solvent, which controls the overall polymer morphology and macroporous structure. Once the template is removed, the product is a heteropolymer network with specific recognition elements for the template molecule.

The network structure depends upon the type of monomer chemistry (i.e., anionic, cationic, neutral, amphiphilic), the association strength and number of interactions between the monomers and template molecule, the association interactions between monomers and pendent groups, the solvent type and the amount of solvent in the mixture, the reactivity ratios of the monomers, and the relative amounts of reacted monomer species in the structure. Since noncovalent forces are weaker than covalent bonds, an increased number of interactions are needed for stable binding and recognition. On a per-bond basis, noncovalent bonds are 1-3 orders of magnitude weaker. Therefore, a greater number of noncovalent bonding with matching structural orientation is needed for aqueous recognition.

A wide variety of polymers may be used to form the heteropolymer network. These include polymers produced by reaction of acrylamides and all their substituted structures including: methacrylamide, ethacrylamide, isopropyl acrylamide, etc., acrylic acid, methacrylic acid, ethacrylic acid, all alkyl acrylic acids, any dicarboxylic acid, such as crotonic acid, phthalic and terephthalic acid any tricarboxylic acid with itself another monomer of the above list (forming a copolymer), two other monomers from the above list (forming terpolymers), or three or more monomers from the above list forming higher order copolymers. The above may be in linear, branched or grafted form, the grafted chains being exclusively one polymer or copolymers of the above, ionically bound or complexed by hydrogen bonds.

The above may be crosslinked in the presence o crosslinking agents to form insoluble but swellable gels or networks, having the ability to absorb water, physiological fluids, buffers or salt solutions with final swelling as low as 1 weight % of water and as high as 99.9% water.

The above crosslinking may be achieved with ethylene glycol dimethacrylate, ethylene glycol diacrylate, ethylene glycol trimethacrylate, ethylene glycol diacrylate, ethylene glycol multi methacrylate where "multi" stands for n=4 to 200 units ethylene glycol multi acrylate where "multi" stands for n=4 to 200 units same as above but propylene glycol multi methacrylate where "multi" stands for n=1 to 200 units same as above but alkylene glycol multi methacrylate where "multi" stands for n=1 to 200 units. One may also use higher order acrylates and methacrylates including but not limited to 1,1,1 trimethylolethane trimethacrylate (TrMETrMA, Molecular Weight 324.4); 1,1,1 trimethylolpropane triacrylate (TrMPTrA, Molecular Weight 296.3); 1,1,1 trimethylolpropane trimethacrylate (TrMPTrMA, Molecular Weight 338.4); pentaerythritol triacrylate (PETrA, Molecular Weight 298.3); glycerol propoxy triacrylate (GlyPTrA, Molecular Weight 428.5); pentaerythritol tetraacrylate (PETeA, Molecular Weight 353.2); ethoxylated 1,1,1 trimethylolpropane triacrylate (ETrMPTrA, Molecular Weight 428); glycerol propoxylated triacrylate (GlyPTrA, Molecular Weight 428) and glycerol trimethacrylate (GlyTrMA, Molecular Weight 396.3). One may also use with "star polymers" or "dendrimers" with up to 72 independent chains ending in acrylates or methacrylates.

The initiator may be Irgacure products of the Ciba Geigy company including Irgacure 184, IRGACURE® 379, Ciba® IRGACURE® 819, and Ciba® IRGACURE® 250. Any other photoinitiator may also be used. The initiator may also be Any peroxide incuding but not limited to benzoyl peroxide, cumyl peroxide, etc. or Azobis isobutyronitrile.

In some embodiments, the biomimetic polymer network of the present disclosure may be formed using a template molecule (e.g., D-glucose) and functional monomers selected to match corresponding templatemolecule (e.g., glucose binding protein residues, such as aspartate, glutamate, and asparagines, as well as biological mechanisms of action that involve recognition The template molecule may be added in stoichiometric amounts in regard to the functionality of the template molecule. Since solvent interaction can stabilize or destabilize binding in noncovalent systems, functional monomers may be selected based on optimizing specific noncovalent, self-assembly interactions (hydrogen bonding) with the template molecule within an aprotic solvent (e.g., dimethylsulfoxide). Such techniques are generally applicable to template molecules, in which hydrogen bonding, hydrophobic, or ionic contributions will direct recognition of the moiety. The formation of an exemplary biomimetic polymer network of the present disclosure according to the methods of the present disclosure is described below.

To facilitate a better understanding of the present disclosure, the following examples of specific embodiments are given. In no way should the following examples be read to limit or define the entire scope of the disclosure.

EXAMPLES

A model biomimetic polymer network of the present disclosure capable of recognizing and binding D-glucose was formed and tested. This model biomimetic polymer network illustrates, among other things, the applicability of the biomimetic polymer networks of the present disclosure for the sustained release of a target compound.

The moiety used was a D-glucose fluorescent analogue, 2-NBDG, which also models the moiety attached to a target compound.

The model biomimetic polymer network was synthesized via biomimetic molecular imprinting techniques using noncovalent complexation interactions, and fluorescent microscopy was utilized as a novel method to characterize the kinetic and equilibrium binding properties of the polymer systems. Specifically, networks based on acrylamide were prepared and characterized using a novel fluorescent microscopy technique, which allowed for microscale observation of the binding and for the direct observation of the analyte uptake within the polymer film. The equilibrium binding characteristics and the kinetic binding and release characteristics of the fluorescent glucose analogue were analyzed.

The relative binding affinity and amount of fluorescent analogue, 2-NBDG, bound within the network was demonstrated to be controlled by the structure and properties of the polymer network. In general, the more rigid networks (shorter crosslinkers and high crosslinking percentages) exhibited higher affinities for 2-NBDG. As crosslinking percentage of the network decreased, the macromolecular recognition of the network chains decreased. Also, as the length of the crosslinker increased, the bound ratio decreased for a given concentration, indicating less imparted affinity. The relative amount of PEG or Aam within the polymer networks did not have a discernible effect on the binding affinity. In addition, 2-NBDG was a model compound to illustrate the applicability of imprinted polymers in novel drug loading and release applications.

D-Glucose Recognitive Network Synthesis

Acrylamide (Aam), 2,2-dimethoxy-2-phenyl acetophenone (DMPA), dimethylsulfoxide (DMSO), ethylene glycol dimethacrylate (EGDMA), and D-glucose, were purchased from Aldrich (Milwaukee, Wis.). PEGnDMA, with n=200, 400, and 600, was obtained from Polysciences, Inc. (Warrington, Pa.). Irgacure® 184, 1-hydroxycyclohexyl phenyl ketone, was purchased from Ciba Specialty Chemicals (Tarrytown, N.Y.). Fluorescent D-glucose analogue, 2-(N-(7-nitrobenz-2-oxa-1,3-diazol-4-yl)amino)-2-deoxy-glucose (2-NBDG), was purchased from Molecular Probes, Inc. (Eugene, Oreg.).

Novel heteropolymer films of differing composition and percentage of crosslinking monomer were synthesized in a aprotic, polar solvent via UV free-radical polymerization in a nitrogen atmosphere. In a typical experiment (e.g. PEG200DMA as crosslinking monomer), 15 mmoles of Aam and 60, 30, or 10 mmoles of PEG200DMA (e.g., 80, 67, or 30% mole crosslinking monomer/mole all monomers, respectively) were allowed to complex with 3 mmoles of D-glucose mixed with 6 mL DMSO. After mixing and checking mutual solubilities, Irgacure® 184 initiator was added in the amount of 1-2 wt %. Control polymers were made with exactly the same composition except D-glucose was not added.

After preparation, the solution was placed in a nitrogen atmosphere and nitrogen was bubbled for 30 minutes to remove oxygen, which is a free-radical scavenger and inhibits the free-radical polymerization. The monomer mixtures were pipetted between two clamped 6" by 6" glass plates with a Teflon® spacer that was 790 microns thick. Next, the glass plate assembly was placed under a UV source (Dymax Ultraviolet Flood Cure System) and exposed to UV light with an intensity of 10.0-15.0 mW/cm$^2$ for 15 minutes to initiate the free-radical polymerization. Polymers were placed in deionized water immediately after preparation, were carefully separated from the slides, and then were cut into various diameter discs using a cork borer. Discs were then placed in 50 mL centrifuge tubes and placed on a rotating mixer (25 RPM, 70 degree angle, Glas-Col, Terre Haute, IN) and resuspended within multiple 24 hour wash steps to remove glucose and excess monomer. The resulting discs were then dried in air at ambient conditions and placed in a vacuum oven (T=26° C., 28 mm Hg vacuum) until a constant weight was obtained (less than 0.1 wt % difference). The discs were then stored in a dessicator until testing.

Analysis of Equilibrium Binding Via Fluorescent Microscopy

Equilibrium binding experiments were conducted to examine the relative equilibrium binding affinity and bound amount of D-glucose within the networks. These studies were conducted utilizing a fluorescent D-glucose analogue, which allowed for microscale observation of the binding and for the direct observation of the uptake within the film. For the characterization of the binding isotherm, a dry polymer disc of known mass was placed in known concentrations of 2-NBDG ($1\times10^{-3}$, $5\times10^{-4}$, $1\times10^{-4}$, and $1\times10^{-5}$ mg/ml) in deionized water. The amount of bound glucose was determined by fluorescent microscopy of the polymer films, and the equilibrium solution concentration was determined by measurement of the resulting supernatant via fluorescent microplate reader (Bio-Tek Instruments, HT Multi-Detection Microplate Reader, Winooski, Vt.).

Equilibrium binding behavior, qualitative and quantitative, was probed by fluorescent microscopy. By analyzing fluorescent intensity values from polymer discs of equal thickness, quantitative analysis of relative amount bound in network can be made. In using fluorescent methods for quantitative analysis, it is critical that all experimental parameters are matched during analysis (objective and field of view, camera integration time, etc.) including excitation times since fluorophore bleaching could drastically alter intensity profiles.

Figure 3:
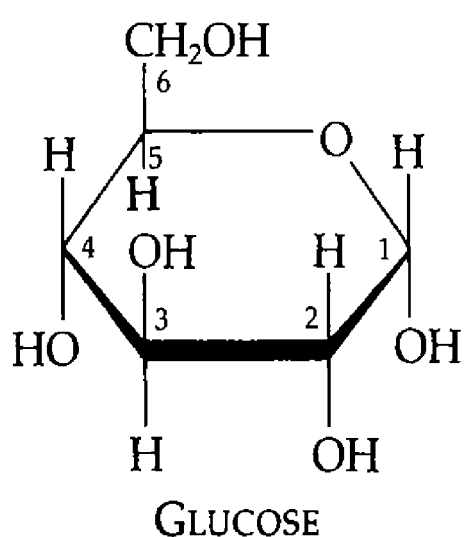
FIG. 3 is a drawing of D-Glucose and its Fluorescent Analogue.
Figure 3:
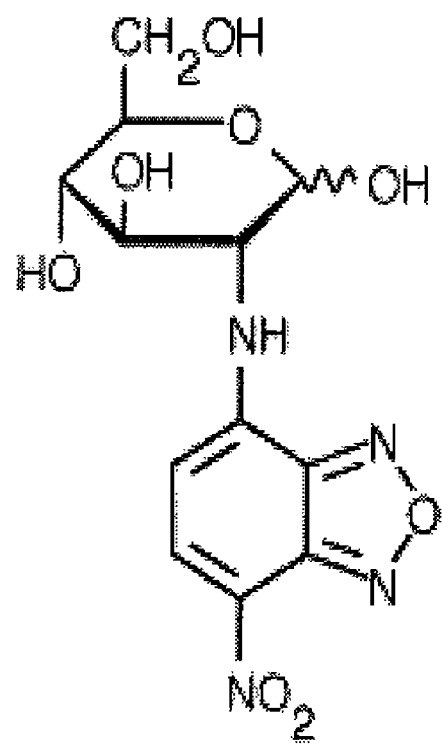

Binding results in water were visualized using 2-NBDG (maximum absorption 466 nm; maximum emission 542 nm) (FIG. 3). An aliquot of known concentration of 2-NBDG ($1\times10^{-4}$ mg/ml ($2.9\times10^{-4}$ mM)) was added to washed, solution-swollen polymer discs in 50 mL of solution within centrifuge tubes. The tubes were covered with aluminum foil and placed on a rotating mixer (Glas-Col., Terre Haute, IN; 70 degree angle, 25 RPM). By analyzing fluorescent intensity values from polymer discs of equal thickness, a histogram of intensity values was obtained, which provided quantitative analysis of binding.

A Nikon Eclipse ME600L fluorescent microscope with a FITC filter set was used and images were acquired with Coolsnap digital camera. Meta-View software from Universal Imaging was utilized to analyze a large amount of pixels within these images for calculation of an average fluorescent intensity and standard deviation across the image.

Results and Discussion of Equilibrium Binding Efficiency

2-NBDG is suitable for analyzing network binding properties. The biomimetic polymer systems studied examined and their identifiers are listed in Table 1.

TABLE 1

| Identifier | Crosslinking % | Crosslinker | EG units per MAA unit | Mole % EG |
|---|---|---|---|---|
| 30-1 | 30 | EGDMA | 0.43 | 30 |
| 30-2 | 30 | PEG200DMA | 1.95 | 66.1 |
| 30-3 | 30 | PEG600DMA | 5.85 | 85.4 |
| 67-1 | 67 | EGDMA | 2 | 67 |
| 67-2 | 67 | PEG200DMA | 9.1 | 90.1 |
| 67-3 | 67 | PEG600DMA | 27.3 | 96.5 |
| 80-1 | 80 | EGDMA | 4 | 80 |
| 80-2 | 80 | PEG200DMA | 18.2 | 94.8 |
| 80-3 | 80 | PEG600DMA | 54.6 | 98.2 |

Figure 4:
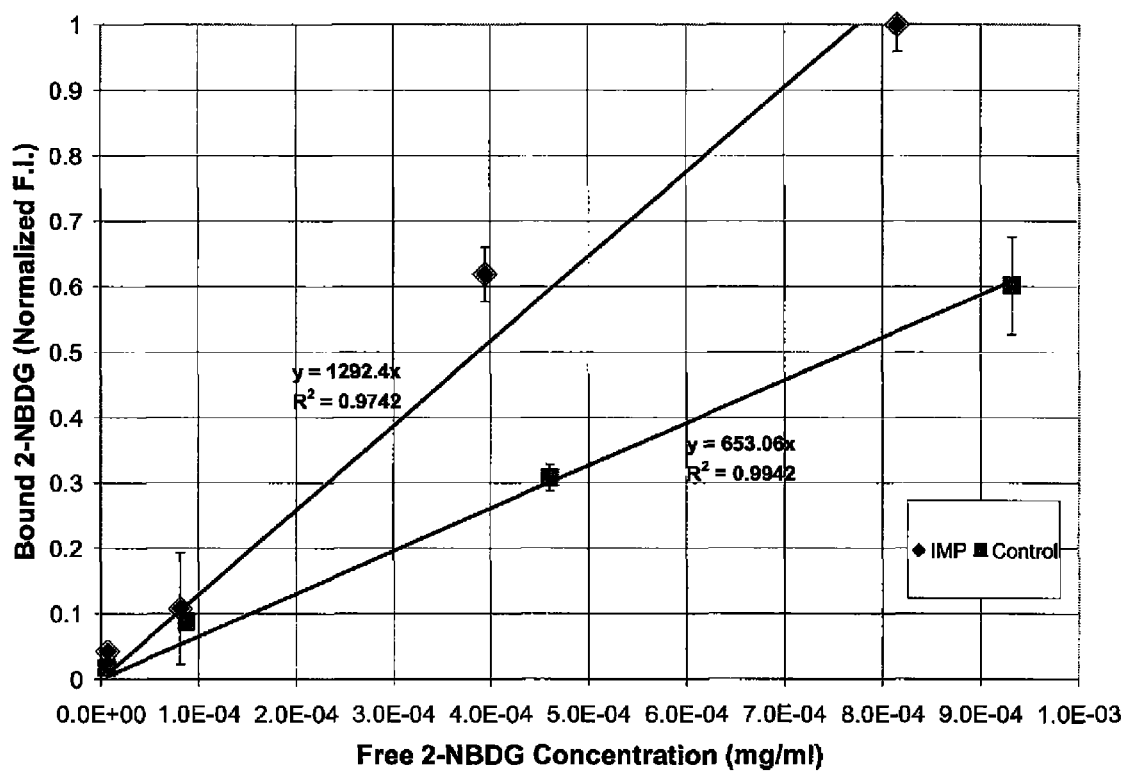
FIG. 4 is a graph of an equilibrium binding isotherm for imprinted (diamonds) and control (squares) networks based on poly(Aam-co-PEG200DMA) networks with a 67% crosslinking percentage.

FIG. 4 presents 2-NBDG binding isotherms for 67-2 and 67-2c, where c indicates control. The concentration of 2-NBDG in the supernatant was measured using the fluorescent microplate reader, and the bound 2-NBDG was measured by fluorescent imaging of the polymer films. The low concentration data fit very well to a linear isotherm, and a linear regression of the data yields the equilibrium association constants. Although the affinity is qualitative and based on a normalized fluorescent intensity, the ratio of imprinted to control, $K_{imprinted}/K_{control}$, is a quantitative measure of the imparted affinity within the imprinted polymer network. The ratio, $K_{imprinted}/K_{control}$, was calculated to be 1.98, which indicated that imprinted network had 1.98 times the affinity for 2-NBDG compared to control networks.

The fluorescent analogue molecule, 2-NBDG, was also applied to determine relative binding affinity for polymer networks with varying crosslinking percent (30, 67, and 80%) and crosslinker length (PEGnDMA, with n of 44, 200, and 600). The relative polymer fluorescent intensity due to the binding of 2-NBDG can be used to determine quantitative binding ratios that are a valuable measure to the affinity of a network for an analyte. In these studies, the 2-NBDG concentration was $1\times10^{-4}$ mg/ml ($2.9\times10^{-4}$ mM).

Figure 5:
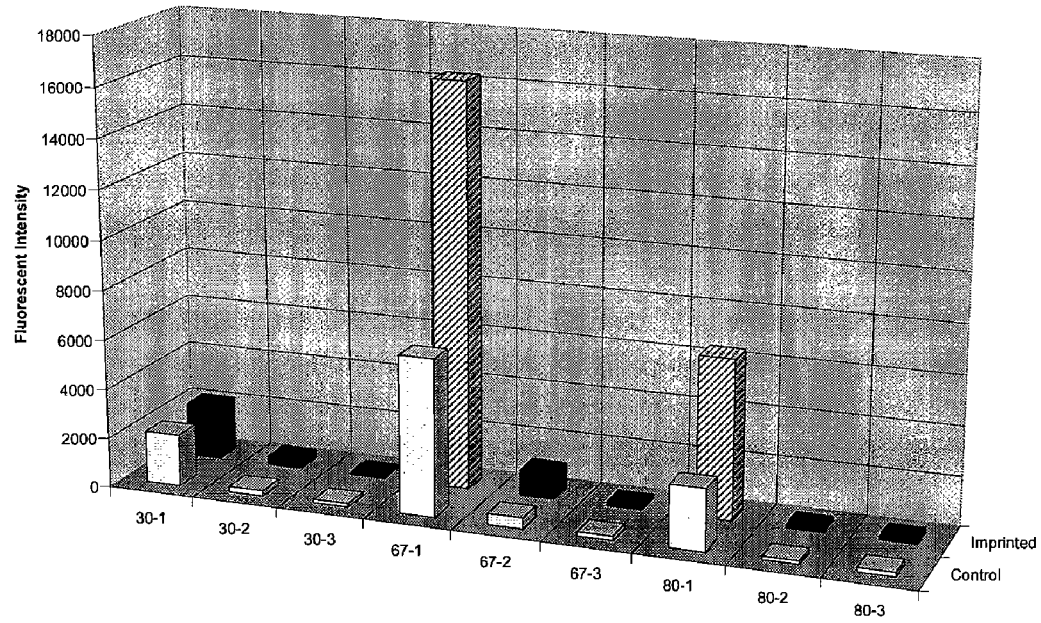
FIG. 5 is a graph showing: (A), the fluorescent intensity, due to uptake of 2-NBDG, of polymer network systems with varying crosslinking percentage and crosslinker length shown, with the values for 67-1, 67-1c, and 80-1 extrapolated from shorter exposure times; and (B), the same data plotted on a smaller scale.
Figure 5:
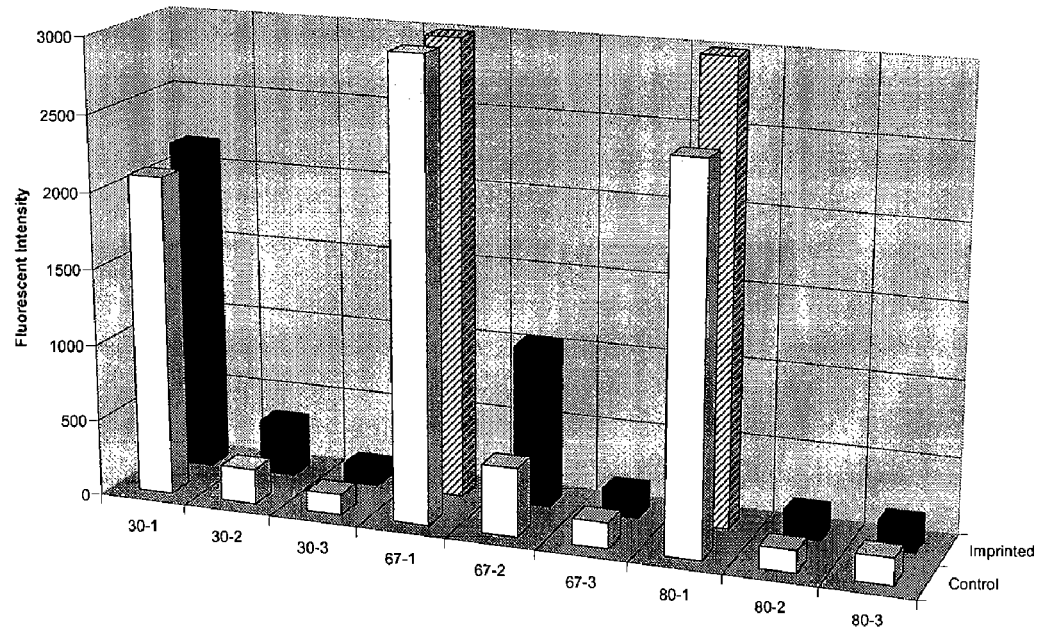
Figure 6:
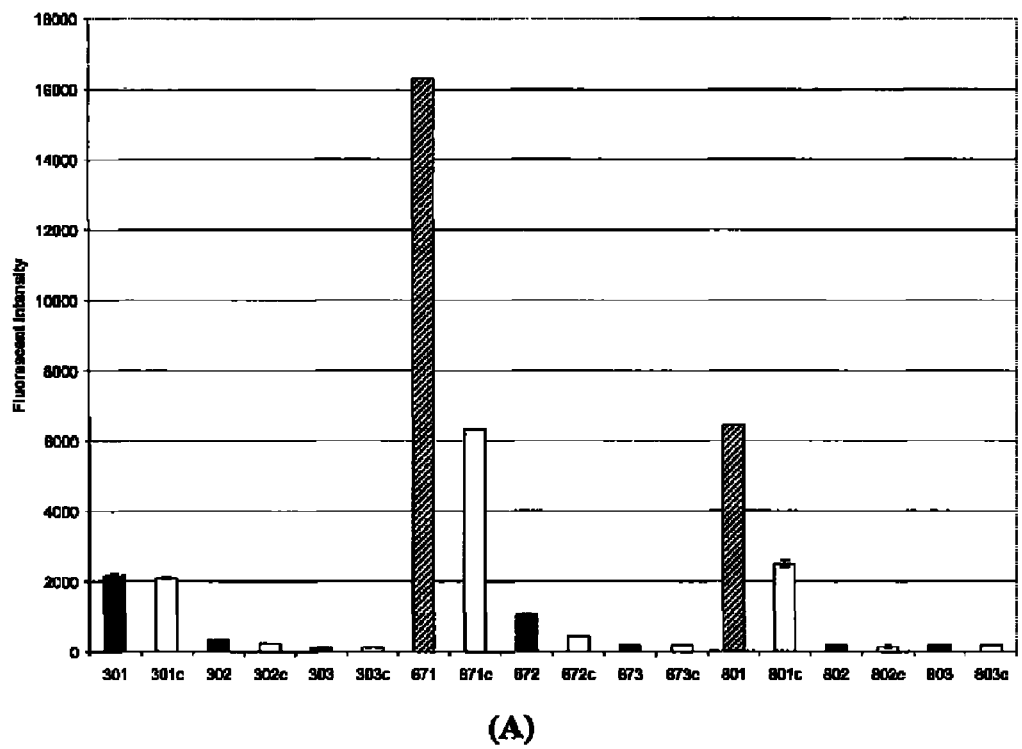
FIG. 6 is a graph showing: (A), the fluorescent intensity, due to uptake of 2-NBDG, of polymer network systems with varying crosslinking percentage and crosslinker length (FIG. 5 data with error bars included); (B), the same data plotted with smaller scale.
Figure 6:
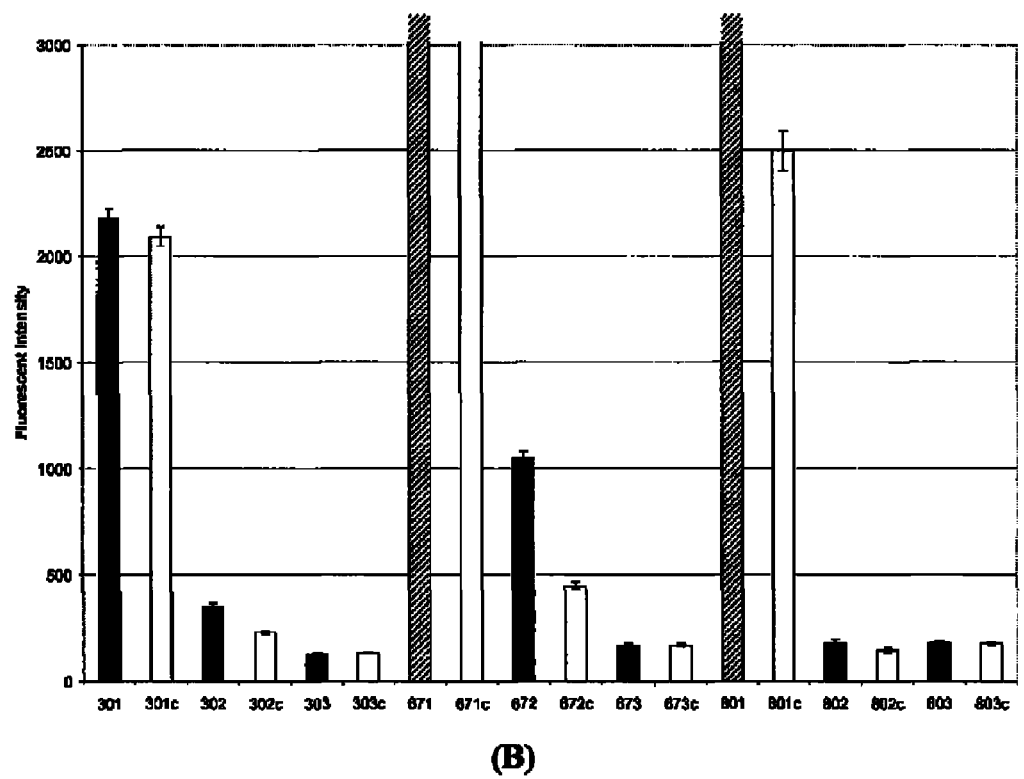

In FIG. 5, the fluorescent intensity due to uptake of 2-NBDG within polymer network systems with varying crosslinking percentage and crosslinker length is presented. The values for 67-1, 67-1c, and 80-1 were extrapolated from values at shorter exposure times. FIG. 6 presents the same data as in FIG. 5 but with error bars included. There are multiple trends that can be observed in this data. First, the increasing the crosslinker length led to lower fluorescent intensities, indicating less 2-NBDG bound to their network. This is a consistent trend in both imprinted and control systems and at each crosslinking percentage. For all crosslinking percentages, the networks crosslinked with EGDMA exhibited the highest fluorescent intensities. The data also illustrates that systems crosslinked with PEG600DMA (30-3, 67-3, and 80-3) bind very little 2-NBDG, and there appears to be no greater affinity imparted to the imprinted systems based on these. It also is shown that for the loosely crosslinked networks (30-1, 30-2, and 30-3) there is little difference between the affinity of the imprinted and control networks and only 30-1 binds significant amounts of 2-NBDG.

Figure 7:
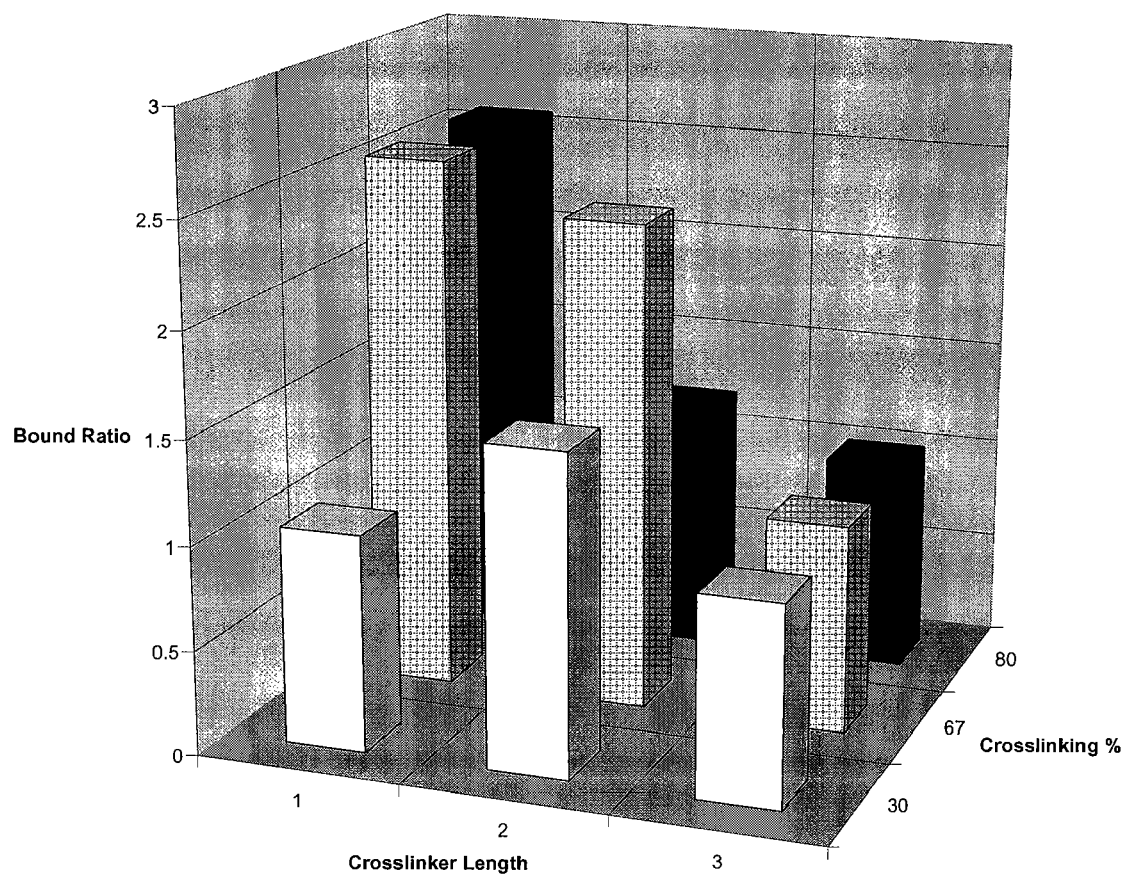
FIG. 7 is a graph showing the bound ratio (ratio of fluorescent intensity due to uptake of 2-NBDG) of polymer network systems with varying crosslinking percentage and crosslinker length.

FIG. 7 presents the bound ratios (ratio of fluorescent intensity due to uptake of 2-NBDG for imprinted networks over control networks) for polymer network systems with varying crosslinking percentage and crosslinker length. These clearly illustrate that the networks crosslinked with PEG600DMA did not exhibit any enhanced affinity for 2-NBDG. This is a result of the lack of rigidity in these networks, which have a looser network structure as a result of the longer crosslinker molecule. Except for the 30% system, there is a clear trend of increasing bound ratio, or affinity enhancement, with decreasing crosslinker length. Therefore, the tighter, more rigid networks tend to exhibit the largest change in affinity resulting from imprinting.

Analysis of Kinetic Binding and Release Via Fluorescent Microscopy

Kinetic binding and release experiments were conducted to examine the relative rates of uptake and release from the polymer networks. The effect of the network structure on the diffusion coefficient of the D-glucose fluorescent analogue, 2-NBDG, was examined. By analyzing fluorescent intensity values from polymer discs of equal thickness, quantitative analysis of relative amount bound in network can be made. An aliquot of known concentration of 2-NBDG ($1\times10^{-4}$ mg/ml ($2.9\times10^{-4}$ mM)) was added to washed, solution-swollen polymer discs (preparation described in section 8.2.1) in 50 mL of solution within centrifuge tubes. The tubes were covered with aluminum foil and placed on a rotating mixer (Glas-Col., Terre Haute, IN; 70 degree angle, 25 RPM). At various time points, kinetic analysis of the binding was carried out. For the release studies, polymer films that had reached equilibrium binding were placed in 50 ml centrifuge tubes filled with DI water. The water was frequently replaced with fresh DI water, allowing for an infinite sink condition to be assumed. Analysis of fluorescent intensity values from polymer discs of equal thickness provided quantitative analysis of binding and release.

A Nikon Eclipse ME600L fluorescent microscope with a FITC filter set was used and images were acquired with Coolsnap digital camera. Meta-View software from Universal Imaging was utilized to analyze a large amount of pixels within these images for calculation of an average fluorescent intensity and standard deviation across the image.

Results and Discussion of Kinetic Binding and Release

Figure 8:
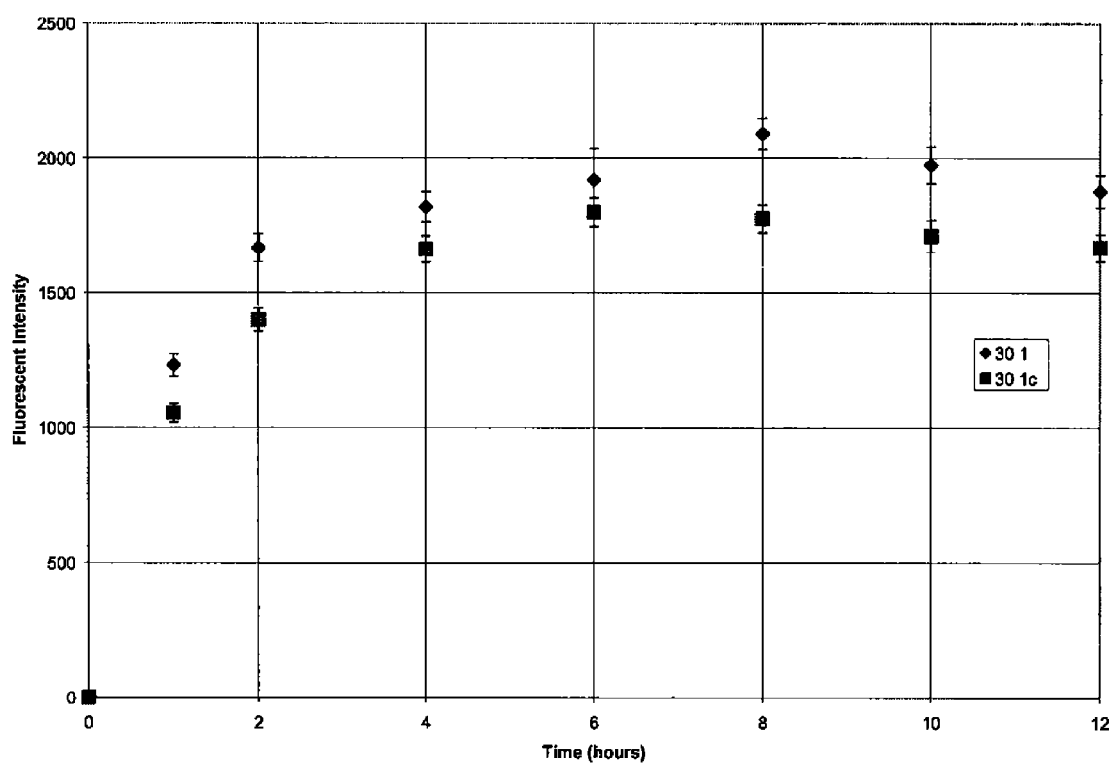
FIG. 8 is a graph showing the kinetic binding results for imprinted and control acrylamide-based polymer systems with 30% EGDMA crosslinking.
Figure 9:
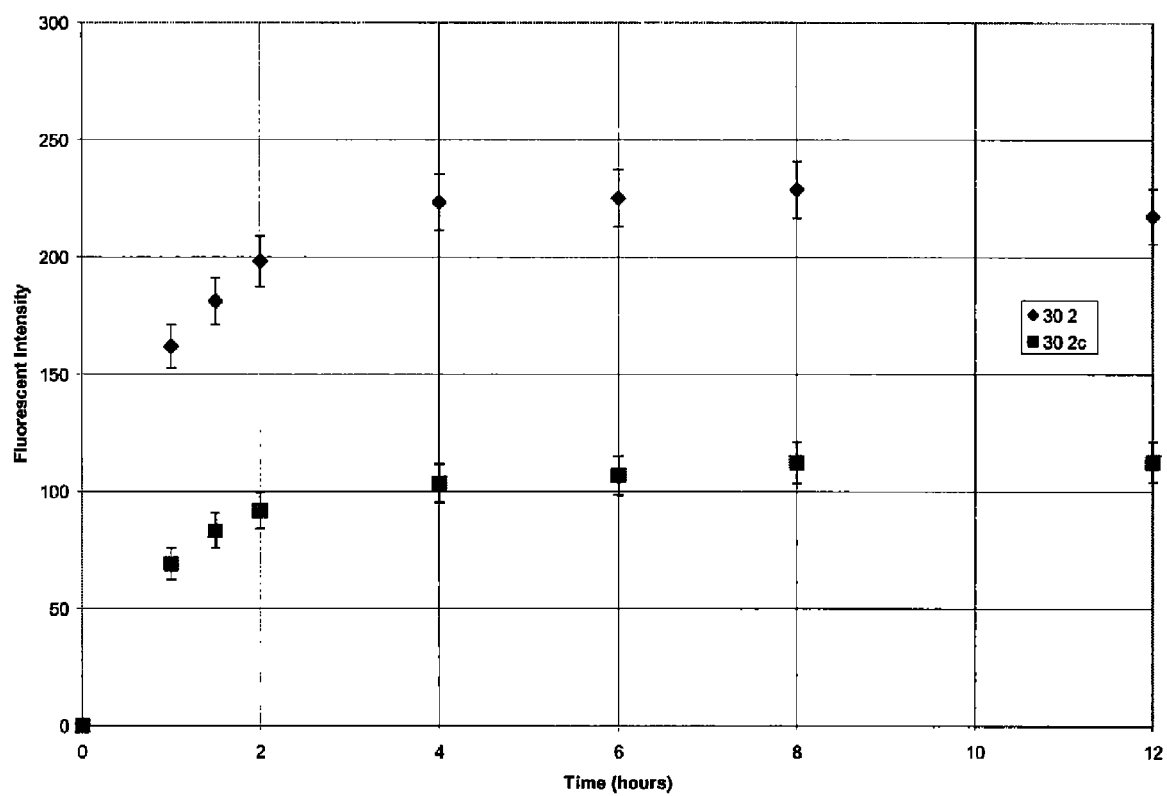
FIG. 9 is a graph showing the kinetic binding results for imprinted and control acrylamide-based polymer systems with 30% PEG600DMA crosslinking.
Figure 10:
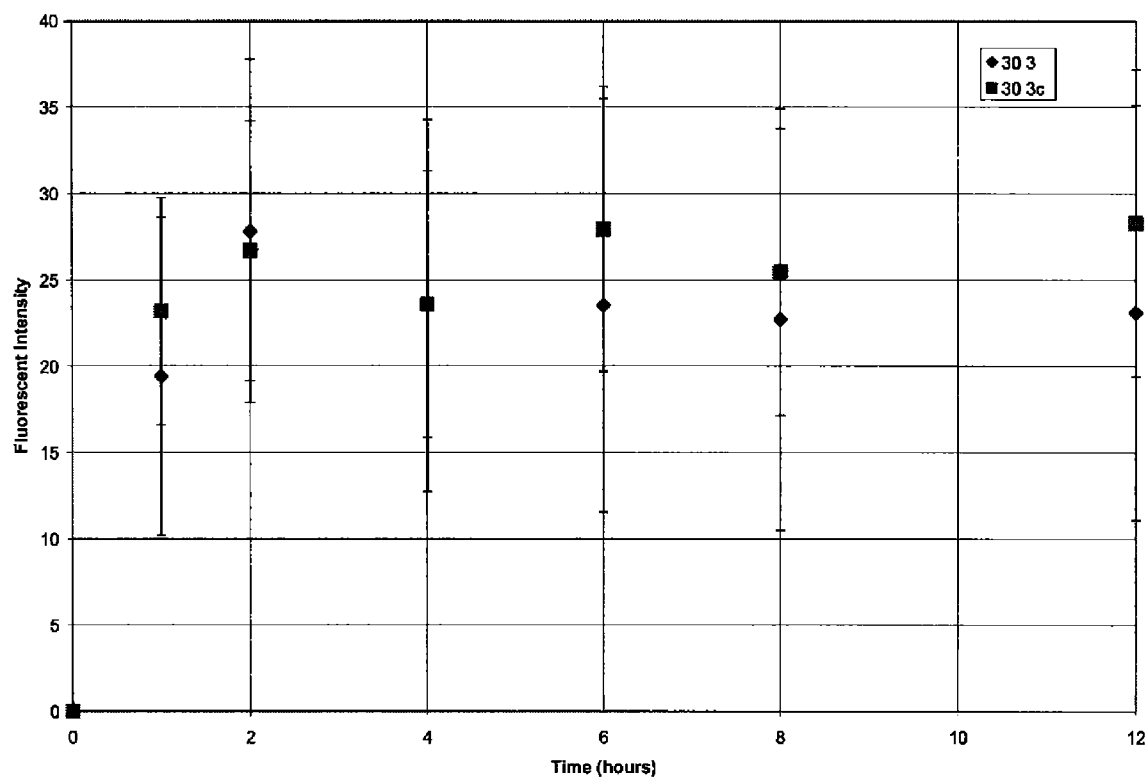
FIG. 10 is a graph showing the kinetic binding results for imprinted and control acrylamide-based polymer systems with 30% PEG600DMA crosslinking.
Figure 11:
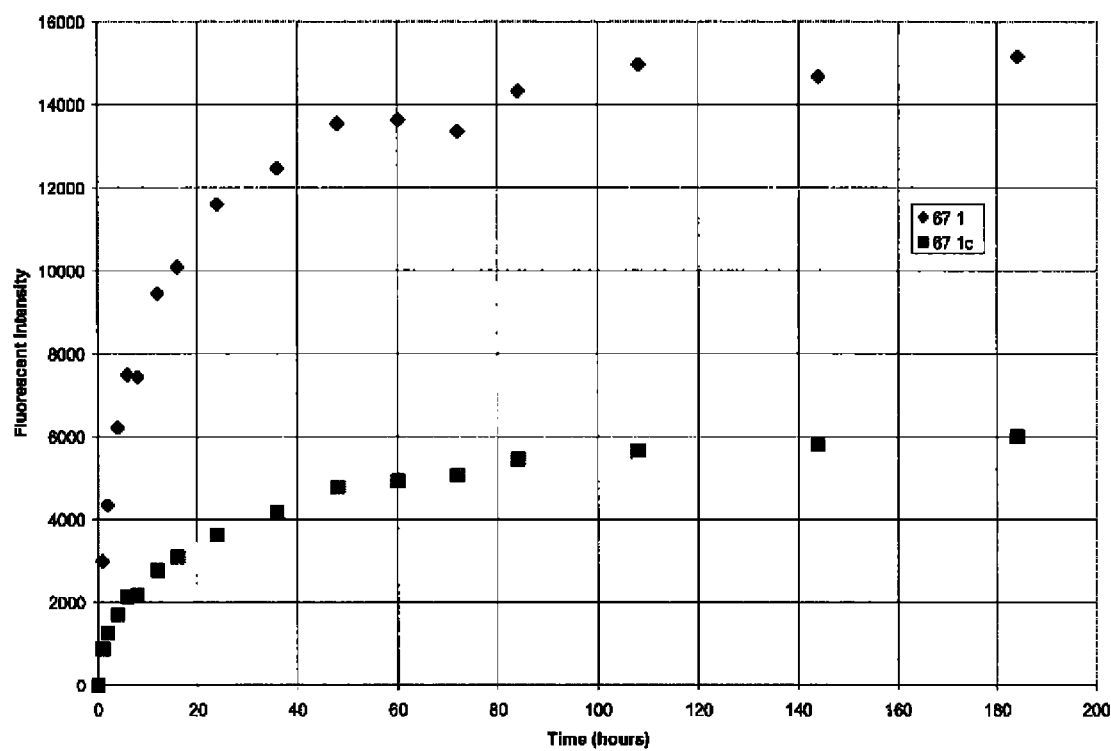
FIG. 11 is a graph showing the kinetic binding results for imprinted and control acrylamide-based polymer systems with 67% EGDMA crosslinking.
Figure 12:
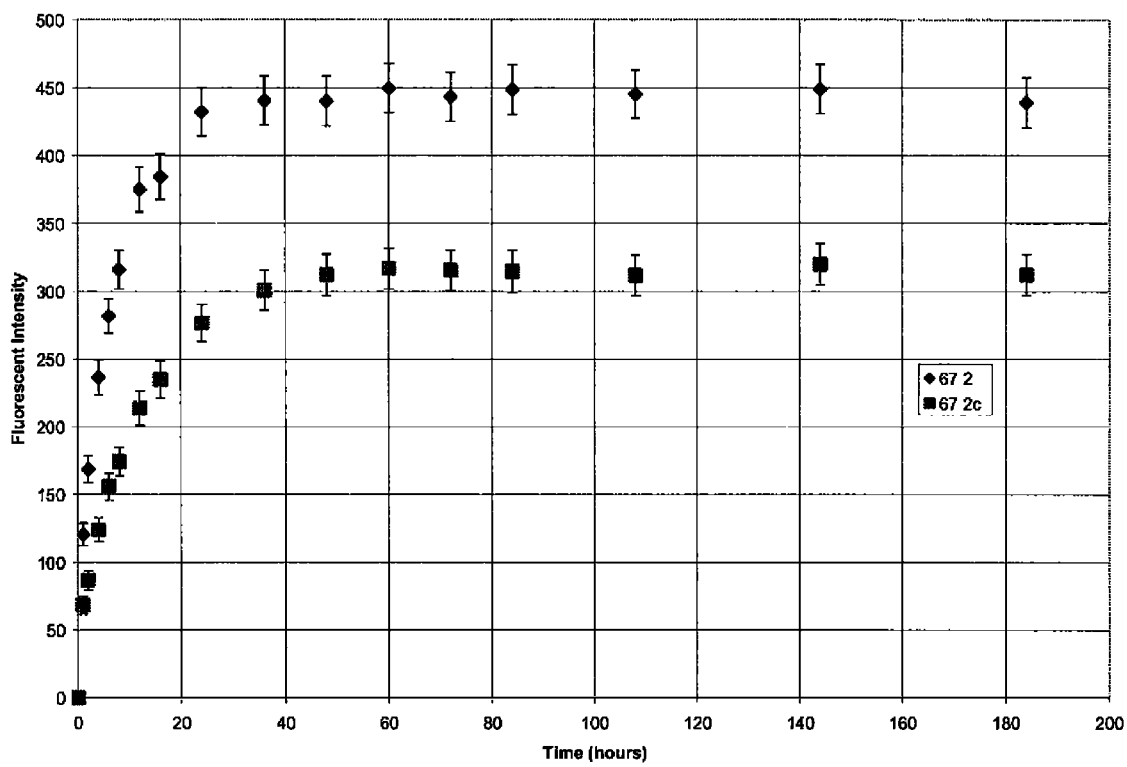
FIG. 12 is a graph showing the kinetic binding results for imprinted and control acrylamide-based polymer systems with 67% PEG200DMA crosslinking of various crosslinker lengths.
Figure 13:
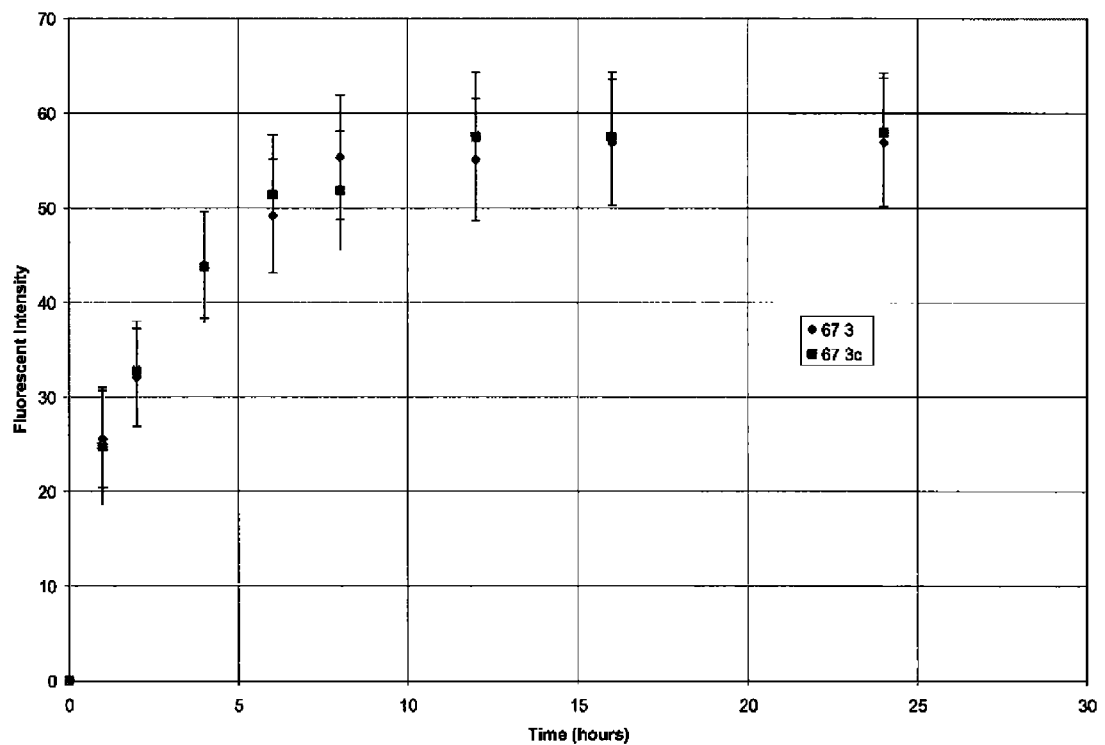
FIG. 13 is a graph showing the kinetic binding results for imprinted and control acrylamide-based polymer systems with 67% PEG600DMA crosslinking.

In FIGS. 8, 9, and 10, kinetic binding results are presented for imprinted and control acrylamide-based polymer systems with 30% crosslinking of various crosslinker lengths (EGDMA in FIG. 9, PEG200DMA in FIG. 10, and PEG600DMA in FIG. 11). It is observed that, as the length of the crosslinker is increased, the time to reach equilibrium binding is decreased. Therefore, the longer crosslinkers result in looser networks, which allow for faster diffusion of the target analyte. FIGS. 11, 12, and 13 present kinetic binding results for imprinted and control acrylamide-based polymer systems with 67% crosslinking of various crosslinker lengths (EGDMA in FIG. 11, PEG200DMA in FIG. 12, and PEG600DMA in FIG. 13). Again, the same trends are observed as were observed for the 30% systems in FIGS. 8, 9, and 10.

For the 67% systems, the power law fit (equation 5.18) and early time fit for Fickian diffusion in a slab geometry (equation 5.24) were applied to determine the power law exponent, n, and the diffusion constant of 2-NBDG in these polymer networks with varying crosslinker length, and these values are included in Table 2. The diffusion analysis for a solute uptake is analogous to that of the solvent uptake. All systems exhibited n values of approximately 0.5, and therefore, can be described by Fickian diffusion. The calculated diffusion constants for the 2-NBDG decreased with decreasing crosslinker length, with the diffusion constant of PEG600DMA network being 5 times larger than for the EGDMA network. For the networks crosslinked with EGDMA and PEG200DMA, the 2-NBDG diffusion constant of the control networks were approximately half of the imprinted networks. This enhancement of the diffusion constants in the imprinted networks is caused by the increased porosity resulting from polymerization in the presence of a template molecule, which acts as a porogen to certain degree. This effect is not observed in the PEG600DMA networks.

TABLE 2

| Identifier | 2-NBDG Diffusion Constant ($\times 10^7$ cm$^2$/s) | Power Law Exponent |
| --- | --- | --- |
| 67-1 | 1.06 | 0.46 |
| 67-1c | 0.53 | 0.46 |
| 67-2 | 2.25 | 0.46 |
| 67-2c | 1.27 | 0.46 |
| 67-3 | 5.37 | 0.39 |
| 67-3c | 5.48 | 0.41 |

Figure 14:
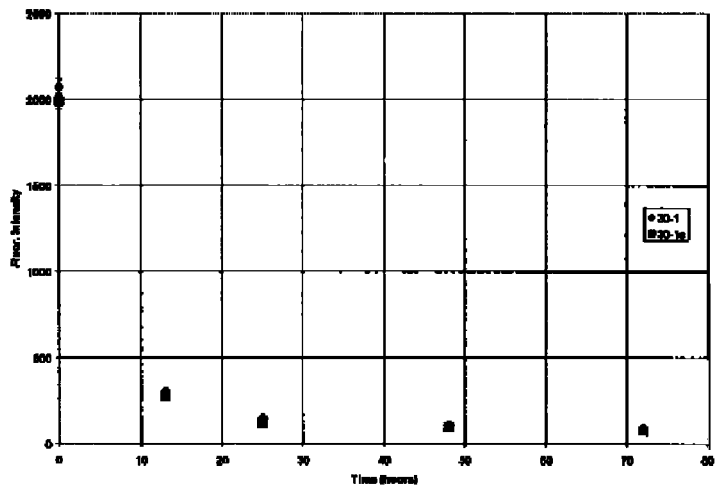
FIG. 14 is a graph showing the kinetic release results for imprinted and control acrylamide-based polymer systems with 30% crosslinking (EGDMA in (A), PEG200DMA in (B), and PEG600DMA in (C)).
Figure 14:
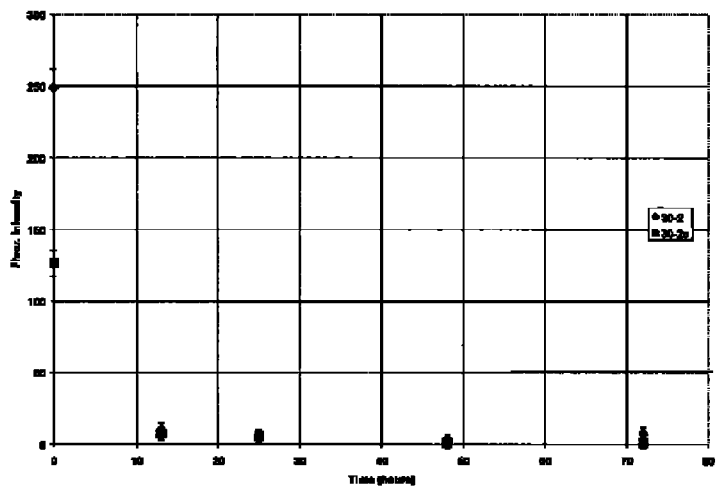
Figure 14:
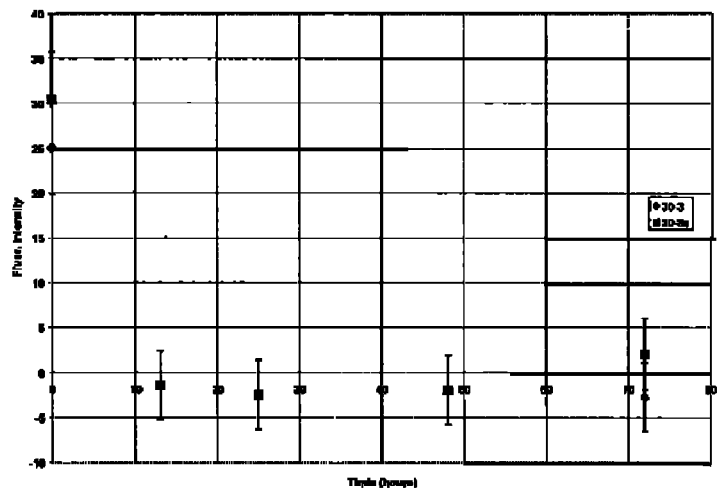
Figure 15:
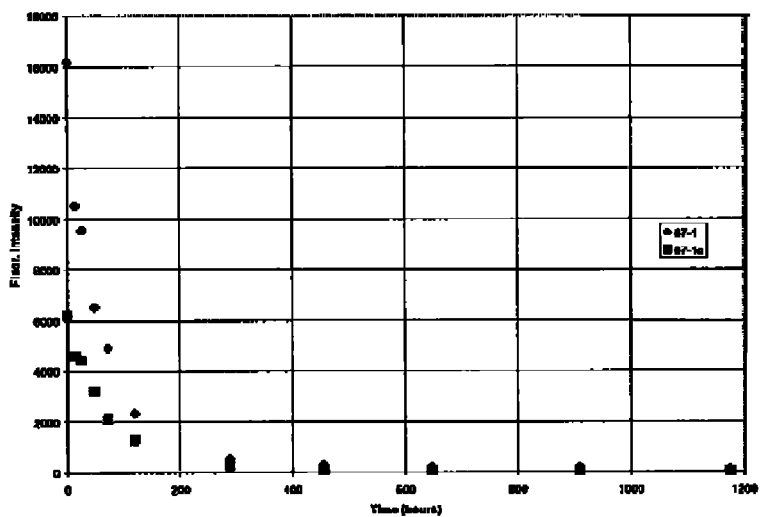
FIG. 15 is a graph showing the kinetic release results for imprinted and control acrylamide-based polymer systems with 67% crosslinking (EGDMA in (A), PEG200DMA in (B), and PEG600DMA in (C)).
Figure 15:
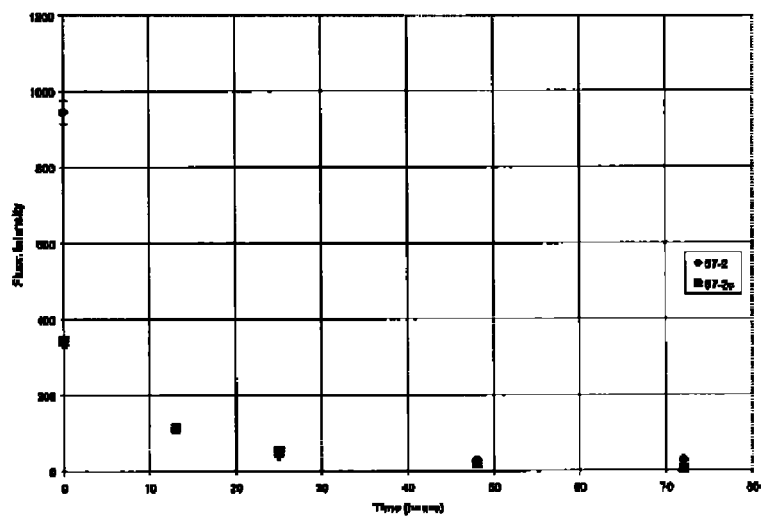
Figure 15:
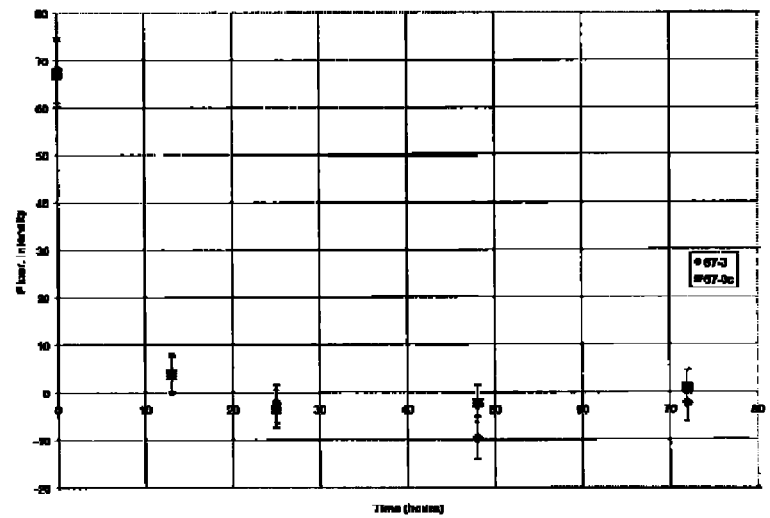
Figure 16:
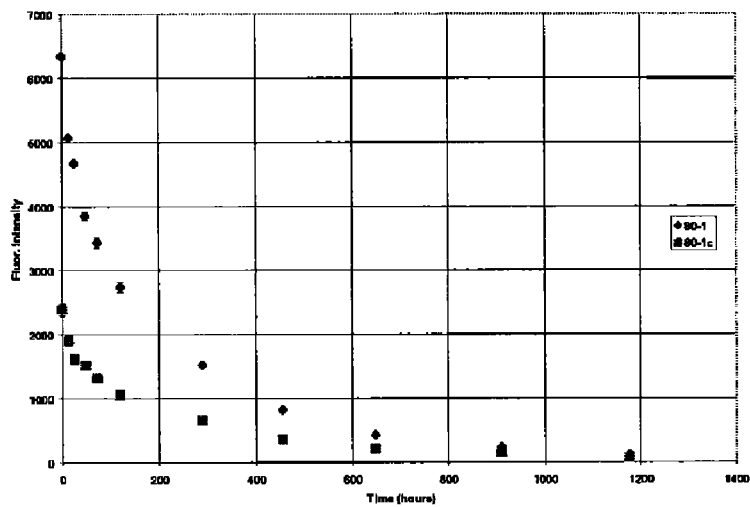
FIG. 16 is a graph showing the kinetic release results for imprinted and control acrylamide-based polymer systems with 80% crosslinking (EGDMA in (A), PEG200DMA in (B), and PEG600DMA in (C)).
Figure 16:
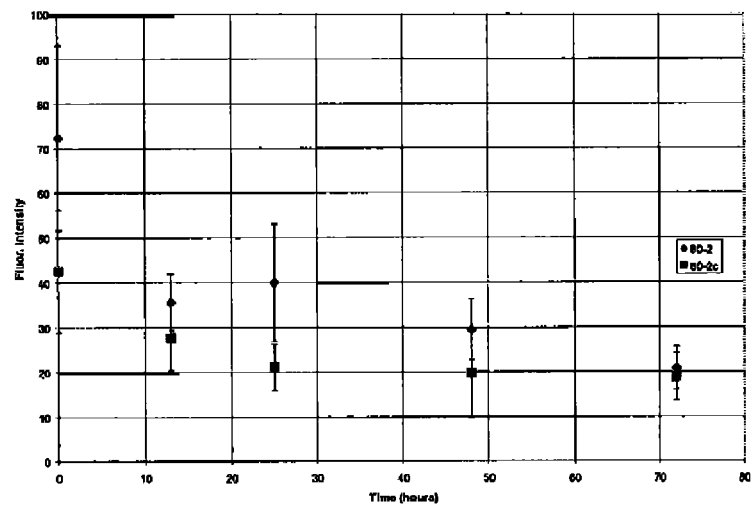
Figure 16:
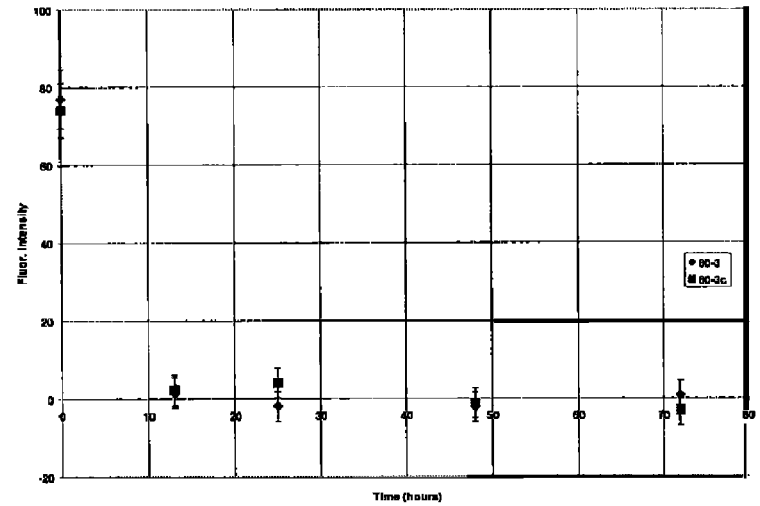
Figure 17:
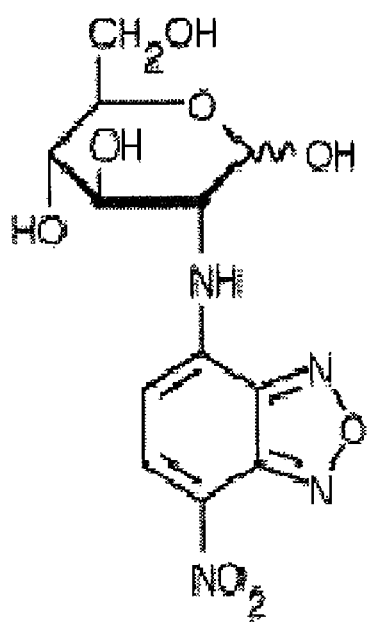
FIG. 17 is a drawing comparing the structure of 2-NBDG and Streptozotocin.
Figure 17:
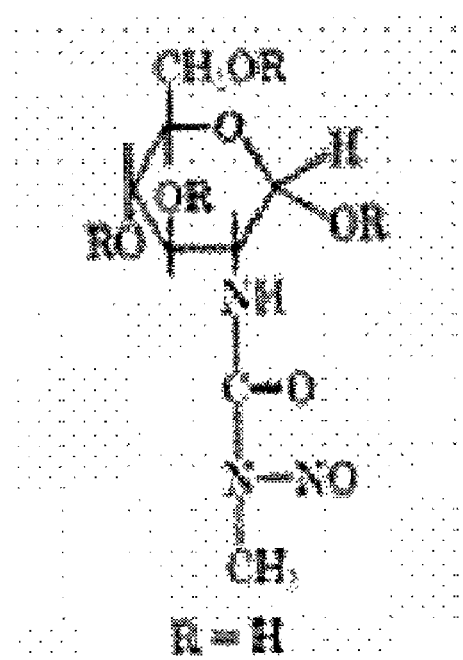

In FIG. 14, kinetic release results for imprinted and control acrylamide-based polymer systems with 30% crosslinking (EGDMA in (a), PEG200DMA in (b), and PEG600DMA in (c)) is presented. All three samples had released most of the bound 2-NBDG within 24 hours. The 30-1 sample exhibited the slowest release, while 30-3 exhibited the fastest release, which is a result of the tighter mesh with shorter crosslinker. In FIG. 15, kinetic release results for imprinted and control acrylamide-based polymer systems with 67% crosslinking (EGDMA in (a), PEG200DMA in (b), and PEG600DMA in (c)) are shown. 67-2 and 67-3 had released most of its bound 2-NBDG within 24 hours, 67-1 still had a significant amount bound after 5 days of washing. Again, there was a clear trend of faster release with longer crosslinker observed. FIG. 16 presents kinetic release results for imprinted and control acrylamide-based polymer systems with 80% crosslinking (EGDMA in (a), PEG200DMA in (b), and PEG600DMA in (c)). Only 80-3 had released most of its bound 2-NBDG within the first 24 hours, while 80-1 still had significant amounts bound after 20 days of release.

Therefore, the present disclosure is well adapted to attain the ends and advantages mentioned as well as those that are inherent therein. While numerous changes may be made by those skilled in the art, such changes are encompassed within the spirit of this disclosure as defined by the appended claims.

The invention claimed is:

1. A biomimetic polymer network comprising a heteropolymer network having a cavity, the cavity having a selective affinity for a moiety, wherein network comprises a copolymer of acrylamide, methacrylamide, ethacrylamide, and isopropyl acrylamide crosslinked with an ethylene glycol dimethacrylate and the moiety comprises glucose.

2. The biomimetic polymer network of claim 1 wherein the cavity and moiety interact through noncovalent binding.

3. The biomimetic polymer network of claim 1 further comprising the moiety.

4. The biomimetic polymer network of claim 1 further comprising the moiety, wherein the moiety is conjugated to a molecule.

5. The biomimetic polymer network of claim 1 further comprising the moiety, wherein the moiety is conjugated to a molecule that is a therapeutic agent, wherein the therapeutic agent comprises hydrocodone.

6. A biomimetic polymer network formed by a process comprising polymerizing a mixture comprising monomers and crosslinkers in the presence of a moiety for which a molecular imprint is to be produced, thereby forming a matrix comprising an imprint of the molecule, and separating the moiety from the matrix, wherein network comprises a copolymer of acrylamide, methacrylamide, ethacrylamide, and isopropyl acrylamide crosslinked with an ethylene glycol dimethacrylate and the moiety comprises glucose.

7. The biomimetic polymer network of claim 6 wherein the mixture comprises a prepolymerization complex, the prepolymerization complex comprising a moiety for which a molecular imprint is to be produced.

8. The biomimetic polymer network of claim 6 wherein the moiety is conjugated to a molecule that is a therapeutic agent, wherein the therapeutic agent comprises hydrocodone.

* * * * *

UNITED STATES PATENT AND TRADEMARK OFFICE
CERTIFICATE OF CORRECTION

PATENT NO. : 7,771,732 B2  
APPLICATION NO. : 11/380803  
DATED : August 10, 2010  
INVENTOR(S) : Nicholas A. Peppas, James Z. Hilt and Mark E. Byrne Page 1 of 1

It is certified that error appears in the above-identified patent and that said Letters Patent is hereby corrected as shown below:

In the Specification

Col. 1, line 13
Replace "This disclosure was developed at least in part using funding from the National Science Foundation, Grant Numbers CTS-03-29317 and DGE-03-33080, and National Institutes of Health, Grant Number EB000246-13A. The U.S. government may have certain rights in the invention." with --This invention was made with government support under Grant no. 0333080 awarded by the National Science Foundation; Grant no. 0329317 awarded by the National Science Foundation; and Grant no. EB000246 awarded by the National Institutes of Health. The government has certain rights in the invention.--

Signed and Sealed this
Sixteenth Day of June, 2015

Michelle K. Lee
*Director of the United States Patent and Trademark Office*